United States Patent [19]
Oliver et al.

[11] Patent Number: 6,022,989
[45] Date of Patent: Feb. 8, 2000

[54] PROCESS FOR THE PREPARATION OF AN ACTIVATED AMINO ACID

[75] Inventors: Patricia A. Oliver, Lindenhurst; Arthur J. Cooper, Lake Villa; Joseph B. Paterson, Jr., Vernon Hills; Denton C. Langridge, Wildwood; Jieh-Heh J. Tien, Libertyville, all of Ill.

[73] Assignee: Abbott Laboratories, Abbott Park, Ill.

[21] Appl. No.: 08/671,893

[22] Filed: Jun. 28, 1996

[51] Int. Cl.$^7$ .................................................... C07C 261/00
[52] U.S. Cl. ........................ 560/132; 560/133; 560/135; 560/136
[58] Field of Search .................................... 560/132, 133, 560/135, 136

[56] References Cited

FOREIGN PATENT DOCUMENTS 9414436  7/1994  WIPO ...................................... 31/425

OTHER PUBLICATIONS

Wutz, et al, Synthesis 622(1989).

*Primary Examiner*—Samuel Barts
*Attorney, Agent, or Firm*—Steven R. Crowley

[57] ABSTRACT

A process is disclosed for the preparation of an N-acylated activated derivative of an amino acid or a salt thereof.

15 Claims, No Drawings

PROCESS FOR THE PREPARATION OF AN ACTIVATED AMINO ACID

TECHNICAL FIELD

The present invention relates to a process for the preparation of an N-acylated activated derivative of an amino acid or a salt thereof.

BACKGROUND OF THE INVENTION

It has recently been determined that HIV protease inhibiting compounds are useful for inhibiting HIV protease in vitro and in vivo and are also useful for inhibiting an HIV (human immunodeficiency virus) infection.

It has also recently been determined that compounds of the formula I:

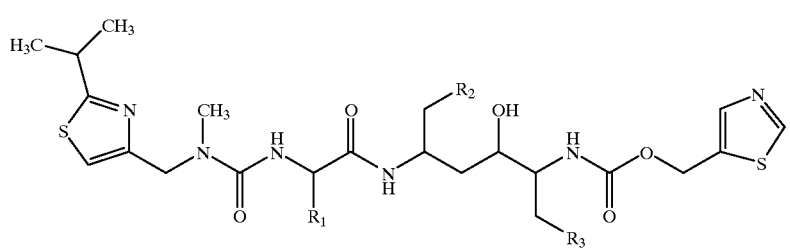

wherein $R_1$ is loweralkyl and $R_2$ and $R_3$ are phenyl are particularly useful as inhibitors of HIV protease and are useful for inhibiting HIV protease in vitro and in vivo and are also useful to inhibit HIV infections.

In particular, the compound of formula II has been found to be especially effective as an inhibitor of HIV-1 protease.

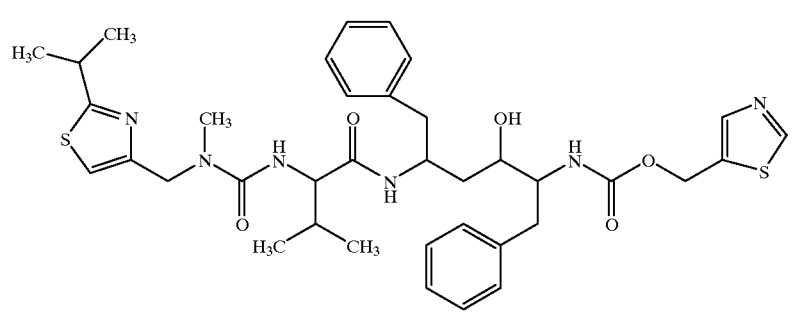

Particularly useful in the preparation of compound of formula is a compound of formula III.

III

The preparation of compounds II and III and the use of compound of as an inhibitor of HIV protease are disclosed in PCT Patent Application No. WO94/14436, published Jul. 7, 1994, which is incorporated herein by reference. The method disclosed for preparing compound III is shown in

I

Scheme 1. This method involves an urea bond forming coupling reaction of intermediates 1 and 2 in the presence of a catalyst such as 4-dimethylaminopyridine and the like to give ester 3. Ester hydrolysis of the valine carboxy protecting group (for example, lithium hydroxide hydrolysis) affords compound III. This process has the disadvantage of including the steps of carboxy protecting and then

II de-protecting the valine residue. A process that avoids protection and deprotection steps would be preferred.

Therefore, there is a continuing need for an improved process for the preparation of III.

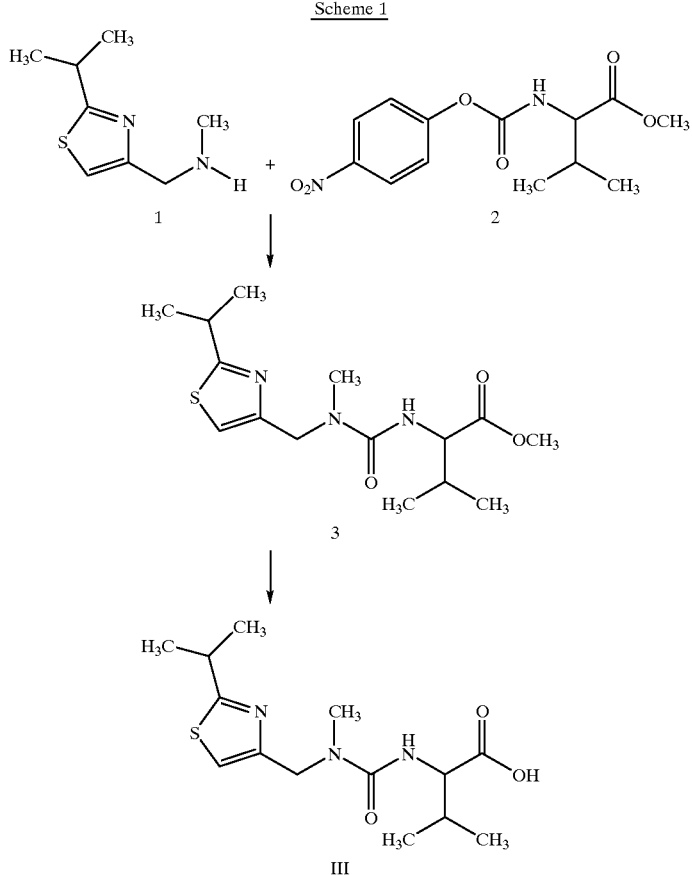

Scheme 1

It has recently been discovered that III can be prepared by reacting amine 4 with carboxylic acid 5, without first protecting the carboxylic acid as the ester (see Scheme 2). Previously, processes for preparing N-acylated activated amino acid derivatives such as 5 typically resulted in the formation of significant amounts of side products such as dipeptides (5a) and acylated dipeptides (5b) (see Scheme 3). Therefore, there is a continuing need for an improved process for the preparation of N-acylated activated amino acid derivatives which will minimize the formation of these unwanted side products.

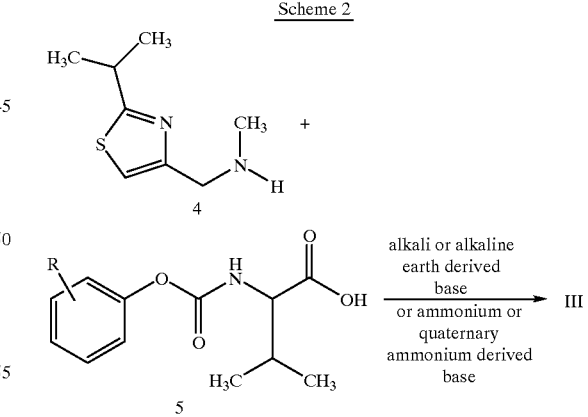

Scheme 2

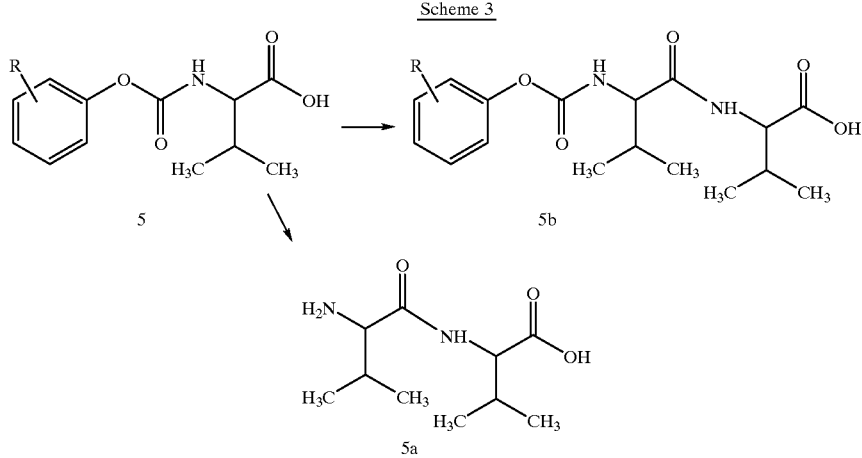

Scheme 3

DISCLOSURE OF THE INVENTION

The present invention relates to a process for the preparation of N-acylated activated amino acid derivatives or salts thereof (compound IV; see Scheme 4)). In particular, the invention relates to a process for the preparation of N-acylated activated derivatives of L-valine ($R_1$ is isopropyl) or salts thereof.

The process of this invention comprises reacting an amino acid 7 with from about 1.05 to about 2.0 molar equivalents (based on 7) of an activated phenyl formate derivative 6 (X is a leaving group, for example, Cl or Br or —$OR_a$ wherein $R_a$ is loweralkyl or —O—$NR_bR_c$ wherein $R_b$ is loweralkyl or —C(O)—loweralkyl and $R_c$ is loweralkyl or —C(O)—loweralkyl, and the like) in water or a mixture of tetrahydrofuran (THF) and water (preferably, a 1:1 mixture) or a mixture of isopropanol and water (preferably, a 1:2 mixture) at a temperature of from about −19° C. to about 25° C. (preferably, from about −19° C. to about −9° C.) at a pH of from about 9.2 to about 10.5 (preferably, from about 9.5 to about 10.5; most preferably, from about 9.8 to about 10.2) in the presence of a base (from about 1.5 to about 4.0 molar equivalents based on 7, preferably, from about 2.0 to about 2.5 molar equivalents based on 7). Preferably, the base is present in sufficient quantity to maintain the pH at from about 9.8 to about 10.2 and, most preferrably, at about pH 10.0. In a preferred embodiment of the invention, a dispersing agent (from about 0.1 to about 220 weight percent based on 7, preferably from about 5 to about 35 weight percent based on 7 and most preferably about 30 weight percent based on 7) is also present.

Scheme 4

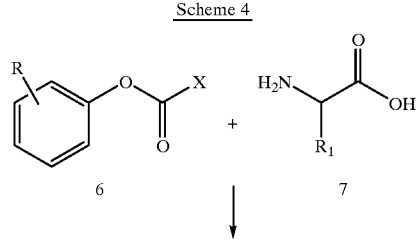

-continued

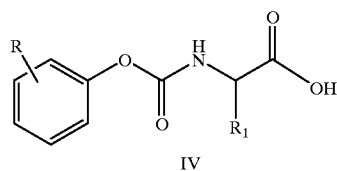

IV

Representative bases which are useful in the process of the invention included lithium hydroxide (LiOH), sodium hydroxide (NaOH), potassium hydroxide (KOH), potassium bicarbonate ($KHCO_3$), magnesium hydroxide ($Mg(OH)_2$), barium hydroxide ($Ba(OH)_2$), magnesium oxide (MgO), lithium carbonate ($Li_2CO_3$), sodium bicarbonate ($NaHCO_3$), sodium carbonate ($Na_2CO_3$), lithium bicarbonate ($LiHCO_3$), potassium carbonate ($K_2CO_3$) and the like. Hydrated bases, where possible, are also useful.

Preferred bases are lithium hydroxide or lithium carbonate.

A most highly preferred base is lithium hydroxide.

Representative dispersing agents which are useful in the process of the invention included lithium carbonate ($Li_2CO_3$), alumina ($Al_2O_3$), diatomaceous earth, sand and the like.

Combinations of dispersing agents, for example, alumina and lithium carbonate, are also useful in the process of this invention.

Preferred dispersing agents are alumina or lithium carbonate.

A most highly preferred dispersing agent is alumina.

In order to obtain the desired reaction temperature without having the reaction mixture freeze, inert non-freezing agents/freezing point depressing agents can be added to the reaction mixture. Such non-freezing agents/freezing point depressing agents include lithium chloride, sodium chloride, potassium chloride and the like. A preferred non-freezing agent/freezing point depressing agent is lithium chloride.

R is selected from the group consisting of hydrogen, loweralkyl, alkenyloxy, alkoxy, alkoxyalkoxy, thioalkoxy and dialkylamino. A preferred substituent R is hydrogen.

$R_1$ is selected from the group consisting of hydrogen, loweralkyl, alkoxyalkyl, hydroxyalkyl, cycloalkyl, cycloalkylalkyl, aryl and arylalkyl. Preferred substituents $R_1$ are loweralkyl. A most prefered substituent $R_1$ is isopropyl.

In the process of this invention, the product can be isolated as the carboxylic acid (for example, by crystallization of the acid form) or as a carboxylate salt.

The term "salt" as used herein refers to an alkali or alkaline earth metal salt or an ammonium or quaternary ammonium salt of a carboxylic acid. Examples of alkali or alkaline earth metals include Li, Na, K, Rb, Cs, Fr, Be, Mg, Ca, Sr, Ba, and Ra.

The term "ammonium or quaternary ammonium cations" as used herein refers to a nitrogen having four substituents and a positive charge. Examples of ammonium and quaternary ammonium cations include ammonium, tetramethylammonium, tetraethylammonium and tetrabutylammonium, as well as other examples described by S. M. Berge, et al., "Pharmaceutical Salts," *J. Pharm. Sci.*, 66:1–19 (1977) which is incorporated herein by reference.

The term "alkenyl" as used herein refers to a straight or branched chain hydrocarbon containing from 2 to 10 carbon atoms and also containing at least one carbon-carbon double bond. Examples of alkenylene include $CH_2=CH-$, $CH_3CH=CH-$, $-C(CH_3)=CH_2$, $CH_3CH=CHCH_2-$, and the like.

The term "alkenyloxy" as used herein refers to $R_5O-$ wherein $R_5$ is an alkenyl group.

The terms "alkoxy" and "thioalkoxy" as used herein refer to $R_6O-$ and $R_6S-$, respectively, wherein $R_6$ is a loweralkyl group.

The term "alkoxyalkoxy" as used herein refers to $R_7O-R_8O-$ wherein $R_7$ is loweralkyl as defined herein and $R_8$ is an alkylenyl group. Representative examples of alkoxyalkoxy groups include methoxymethoxy, ethoxymethoxy, t-butoxymethoxy and the like.

The term "alkoxyalkyl" as used herein refers to an alkoxy group appended to a loweralkyl radical.

The term "alkoxycarbonyl" as used herein refers to $R_9C(O)-$ wherein $R_9$ is an alkoxy group.

The term "alkylenyl" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "aryl" as used herein refers to a mono- or bicyclic carbocyclic ring system comprising 6 to 12 carbon atoms and having one or two aromatic rings including, but not limited to, phenyl, naphthyl, tetrahydronaphthyl, indanyl, indenyl and the like. Aryl groups can be unsubstituted or substituted with one, two or three substituents independently selected from loweralkyl, halo, haloalkyl, alkoxy, alkoxycarbonyl, thioalkoxy, dialkylamino, nitro, carboxaldehyde and cyano.

The term "arylalkyl" as used herein refers to an aryl group as previously defined, appended to a loweralkyl radical, for example, benzyl and the like.

The term "cycloalkyl" as used herein refers to an aliphatic ring system having 3 to 8 carbon atoms including, but not limited to, cyclopropyl, cyclopentyl, cyclohexyl, and the like.

The term "cycloalkylalkyl" as used herein refers to a cycloalkyl group appended to a loweralkyl radical, including but not limited to cyclohexylmethyl.

The term "dialkylamino" as used herein refers to $-NR_{10}R_{11}$ wherein $R_{10}$ and $R_{11}$ are independently selected from loweralkyl groups.

The term "halo" or "halogen" as used herein refers to $-Cl$, $-Br$, $-I$ or $-F$.

The term "haloalkyl" as used herein refers to a loweralkyl group in which one or more hydrogen atoms are replaced by halogen, for example, chloromethyl, chloroethyl, trifluoromethyl and the like.

The term "hydroxyalkyl" as used herein refers to a loweralkyl radical to which is appended an hydroxy group.

The terms "loweralkyl" or "alkyl" as used herein refer to straight or branched chain alkyl radicals containing from 1 to 10 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "dispersing agent" as used herein refers to an inert material which is added to the reaction mixture to prevent clumping/aggregation of the reagents in the reaction mixture. Such agents can be insoluble or soluble in the reaction mixture. Preferred dispersing agents are insoluble in the reaction mixture.

The following examples will serve to further illustrate the process of the invention.

EXAMPLE 1

N-phenoxycarbonyl-L-Valine

Into a 3000 mL jacketed flask equipped with an overhead stirrer, chiller, pH probe and thermocouple was added 500 mL of distilled water, lithium chloride (50 g, 1.18 moles), L-valine (80.0 g, 0.68 moles) and neutral alumina (10.0 g, 150 mesh, Aldrich). The heterogeneous mixture was stirred and cooled to −10°C. At −10° C., the pH was adjusted from 6.8 to 9.5 with 10% aqueous lithium hydroxide. Phenylchlorformate (90.0 mL, 112.0 g, 0.72 moles) was added and the pH was controlled during the reaction using a continuous addition of lithium hydroxide (60.0 g in 450 mL of distilled water). The pH was thus maintained between about 9.0 and about 9.5.

The reaction was stirred for 4 hours at about −10° C. The product was filtered and washed with 500 mL of distilled water. The aqueous filtrate was extracted with methyl t-butyl ether(500 mL) to remove residual phenol. The aqueous phase was then extracted at 0–5° C. into 800 mL of toluene after adjusting the pH to about 1.8–2.0 with 25% sulfuric acid. The aqueous phase was back-extracted with toluene (400 mL) and the toluene phases were combined and concentrated under vacuum (<45° C.) to yield a clear oil.

To the oil was added 320 mL of toluene and 240 mL of heptane. After dissolving the oil at <40° C., the heat was removed and the solution was stirred overnight. After 16 hours, the resulting white slurry was filtered and the solid was washed with 120 mL of 50:50 toluene/heptane. The product was dried for about 8 hours at 45–50° C. until constant weight was obtained, providing the desired product as a white solid. m.p. 84.5–85.5° C. IR 1690 cm$^{-1}$ (C=O), 1718 cm$^{-1}$ (C=O).

EXAMPLE 2

Alternate Preparation of N-phenoxycarbonyl-L-Valine

Into a 1000 mL jacketed flask equipped with an overhead stirrer, chiller, pH probe and thermocouple was added 157 mL of distilled water, lithium chloride (15.5 g, 0.37 moles), L-valine (25.0 g, 0.21 moles) and neutral alumina (7.8 g, 150 mesh, Aldrich). The heterogeneous mixture was stirred and cooled to −13° C. At −13° C., the pH was adjusted from 6.8 to 10.0 with 10% aqueous lithium hydroxide. Precooled (−20° C.) phenylchlorformate (28.2 mL, 35.2 g, 0.22 moles) was added and the pH was controlled during the reaction using a continuous addition of lithium hydroxide (20.0 g in 150 mL of distilled water). The pH was thus maintained between about 9.8 and about 10.2.

The reaction was stirred for 2 hours at about −13° C., followed by stirring for 2 hours at about −10° C. The product was filtered and washed with 160 mL of distilled water. The aqueous filtrate was extracted with methyl t-butyl ether (160 mL) to remove residual phenol. The aqueous phase was then extracted at 0–5° C. into 250 mL of toluene after adjusting the pH to about 1.8–2.0 with 25% sulfuric acid. The aqueous phase was back-extracted with toluene (125 mL) and the toluene phases were combined and concentrated under vacuum (<45° C.) to yield a clear oil.

To the oil was added 100 mL of toluene and 75 mL of heptane. After dissolving the oil at <40° C., the heat was removed and the solution was stirred overnight. After 16 hours, the resulting white slurry was filtered and the solid was washed with 40 mL of 50:50 toluene/heptane. The product was dried for about 8 hours at 45–50° C. until constant weight was obtained, providing the desired product as a white solid.

EXAMPLE 3

Alternate Preparation of N-phenoxycarbonyl-L-Valine

Into a 1000 mL jacketed flask equipped with an overhead stirrer, chiller, pH probe and thermocouple was added 200 mL of distilled water, lithium carbonate (37.8 g, 0.51moles) and L-valine (20.0 g, 0.17 moles). The heterogeneous mixture was stirred and cooled to 0–2° C. At 0° C., pH 9.79, phenylchlorformate (42.7 mL, 53.2 g, 0.34 moles) was added and the pH was controlled during the reaction using a continuous addition of lithium hydroxide (27.9 g in 223 mL of distilled water). The pH was thus maintained between about 9.5 and about 10.5.

The reaction was stirred for 4 hours at about 0° C. 80 mL of methyl t-butyl ether was added to the reaction mixture and stirred for 15 minutes. The residual salts were filtered off and washed with 40 mL of water and 40 mL of methyl t-butyl ether. The filtrate was warmed to room temperature, the phases were separated and the aqueous phase was washed with 80 mL of methyl t-butyl ether.

The aqueous phase was cooled to 0–5° C., 200 mL of toluene was added the biphasic mixture was stirred and acidified to pH 1.8–2.0 with the addition of dilute sulfuric acid (12.0 mL of sulfuric acid in 48 mL of distilled water), while maintaining the temperature at 0–5° C. At pH 1.67, the reaction was warmed to room temperature and the layers were separated. The aqueous phase was washed with toluene (2×100 mL) and the combined toluene phases were concentrated under vacuum at <50° C.

The resulting residue was dissolved in 80 mL of toluene and 60 mL of heptane and warmed to 40° C. to dissolve. The solution was seeded with crystals of the desired product and the resulting cloudy mixture was stirred overnight. The resulting thick white slurry was filtered and the solid was washed with 24 mL of 50:50 toluene/heptane. The solid was dried at 45–50° C. overnight to provide the desired product as a white solid (34.02 g).

EXAMPLE 4

Alternate Preparation of N-phenoxycarbonyl-L-Valine

Into a reactor equipped with an overhead stirrer, chiller, pH probe and thermocouple was added lithium chloride (15.6 kg, 368 moles), L-valine (26.0 kg, 222 moles), neutral alumina (8.1 kg, 150 mesh, Aldrich) and 156 kg of distilled water. The heterogeneous mixture was stirred and cooled to −14° C.±5° C. The pH was adjusted to 10.1 with 10% aqueous lithium hydroxide. Precooled (−20° C.) phenylchlorformate (36.6 kg, 234 moles) was added while maintaining a temperature of not more than −9° C. and the pH was controlled during the reaction (maintaining a pH within the range of 9.5 to 10.5 with a target of 10.0) using a continuous addition of 10% aqueous lithium hydroxide.

The reaction was stirred for 2 hours at about −14° C. The reaction mixture was filtered through Celite and the filter cake was washed with 42 kg of distilled water. The aqueous filtrate was extracted with methyl t-butyl ether (65 kg) to remove residual phenol. The aqueous phase was then cooled to 0–5° C. and mixed with 200 kg of toluene. The stirred biphasic solution was adjusted to pH 1.8–2.0 with 25% (w/w) sulfuric acid. The toluene layer was concentrated at not more than 40° C. to approximately 120 L, filtered (30 kg rinse of toluene) and then concentrated again at not more than 40° C. to approximately 120 L.

To the resulting solution was added 44.2 kg of heptane and the resulting solution was heated to 40° C.±10° C. for 15 minutes. The heat was removed and the solution was seeded and stirred overnight. The product crystallized on the walls of the reactor and was resuspended in 80 kg of toluene, reconcentrated at not more than 50° C. to approximately 130 L, then 45.2 kg of heptane was added. The resulting solution was then heated to 40° C.±10° C. for not less than 15 minutes and then cooled at not more than 20° C./hour to 18° C.±5° C. After not less than 12 hours, the resulting white slurry was cooled to 14° C.±5° C. and stirred for not less than 3 hours. The white slurry was filtered and the solid washed with 41 kg of 1:1 toluene/heptane. The solid product was dried at not more than 50° C. to provide the desired product (47.8 kg) as a white powder.

EXAMPLE 5

N-((N-Methyl-N-((2-isopropyl-4-thiazolyl)methyl)amino)carbonyl)-L-Valine

To a suspension of LiOH monohydrate (1.06 g, 25.2 mmol) in THF (20 mL) at 0° C. to 5° C. was added 3.78 g (22.2 mmol) of N-methyl-N-((2-isopropyl-4-thiazolyl)methyl)amine, followed by a 5 mL THF rinse. To this solution was added a solution of N-phenoxycarbonyl-L-Valine (5.0 g, 21.1 mmol) in 20 mL of THF. Following a 5 mL THF rinse, 0.5 mL of water was added, and the reaction mixture was allowed to warm to 20° C. with stirring. After 6 hours, the reaction was cooled to 10° C. and quenched with water (55 mL). The THF was removed under reduced pressure, MTBE (50 mL) was added, and the biphasic solution was adjusted to pH 9.0 with 4 N HCl. The layers were separated and the aqueous layer was washed with an additional 50 mL of MTBE. The aqueous layer was sitrred with 130 mL of toluene and adjusted to pH 3 with 4 N HCl, and the phases were separated. The aqueous, product-containing layer was stirred with 50 mL of toluene and adjusted to pH=3.0 with 4N HCl. The aqueous layer was separated and extracted once more with 50 mL of toluene. The combined organic extracts were concentrated in vacuo. The residue obtained was redissolved in toluene, filtered and rinsed with toluene (approx. 50 mL total). The combined filtrates were concentrated in vacuo to an oil. Toluene (25 mL) and heptane (25 mL) were added and warmed to 50° C. The clear solution was allowed to cool until cloudy and then was seeded with N-((N-Methyl-N-((2-isopropyl-4-thiazolyl)

methyl)amino)carbonyl)-L-Valine. The resulting slurry was stirred for at least 12 hours and the product was collected by filtration and washed with heptane (5 mL). The resulting solid was dried in a vacuum oven at 50° C. to yield the desired product as a white powder.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of a compound of the formula:

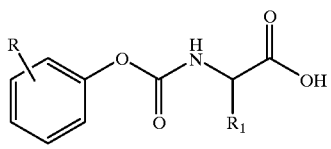

or a salt thereof, wherein R is selected from the group consisting of hydrogen, loweralkyl, alkenyloxy, alkoxy, alkoxyalkoxy, thioalkoxy and dialkylamino and $R_1$ is selected from the group consisting of hydrogen, loweralkyl, alkoxyalkyl, hydroxyalkyl, cycloalkyl, cycloalkylalkyl, aryl and arylalkyl, comprising reacting a compound of the formula:

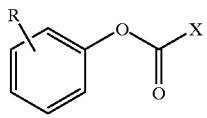

wherein R is as defined above and X is a leaving group with a compound of the formula:

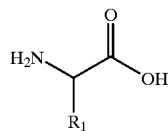

wherein $R_1$ is as defined above, in the presence of a base at a pH of from about 9.2 to about 10.5.

2. The process of claim 1 wherein R is hydrogen, $R_1$ is loweralkyl and X is Cl.

3. The process of claim 1 wherein the base is selected from the group consisting of LiOH, NaOH, KOH, $KHCO_3$, MgO, $Li_2CO_3$, $NaHCO_3$, $Na_2CO_3$, $LiHCO_3$ and $K_2CO_3$.

4. The process of claim 1 wherein the pH is from about 9.5 to about 10.5.

5. A process for the preparation of a compound of the formula:

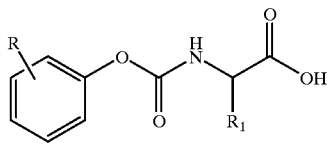

or a salt thereof, wherein R is selected from the group consisting of hydrogen, loweralkyl, alkenyloxy, alkoxy, alkoxyalkoxy, thioalkoxy and dialkylamino and $R_1$ is selected from the group consisting of hydrogen, loweralkyl, alkoxyalkyl, hydroxyalkyl, cycloalkyl, cycloalkylalkyl, aryl and arylalkyl, comprising reacting a compound of the formula:

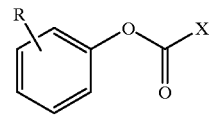

wherein R is as defined above and X is a leaving group with a compound of the formula:

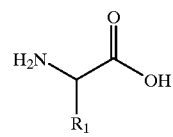

wherein $R_1$ is as defined above, in the presence of a base and a dispersing agent at a pH of from about 9.2 to about 10.5.

6. The process of claim 5 wherein R is hydrogen, $R_1$ is loweralkyl and X is Cl.

7. The process of claim 5 wherein the base is selected from the group consisting of LiOH, NaOH, KOH, $KHCO_3$, MgO, $Li_2CO_3$, $NaHCO_3$, $Na_2CO_3$, $LiHCO_3$ and $K_2CO_3$.

8. The process of claim 5 wherein the dispersing agent is selected from the group consisting of alumina, $Li_2CO_3$, diatomaceous earth and sand or combinations thereof.

9. The process of claim 5 wherein the pH is from about 9.5 to about 10.5.

10. A process for preparing a compound of the formula:

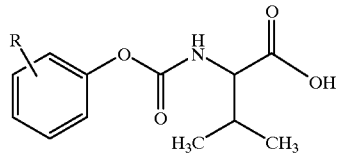

or a salt thereof, wherein R is selected from the group consisting of hydrogen, loweralkyl, alkenyloxy, alkoxy, alkoxyalkoxy, thioalkoxy and dialkylamino, comprising reacting a compound of the formula:

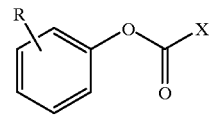

wherein R is as defined above and X is a leaving group with a compound of the formula:

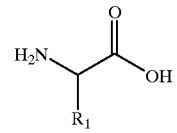

wherein $R_1$ is isopropyl, in the presence of a base and a dispersing agent at a pH of from about 9.2 to about 10.5.

11. The process of claim 10 wherein R is hydrogen and X is Cl.

12. The process of claim 10 wherein the base is selected from the group consisting of LiOH, NaOH, KOH, KHCO$_3$, MgO, Li$_2$CO$_3$, NaHCO$_3$, Na$_2$CO$_3$, LiHCO$_3$ and K$_2$CO$_3$.

13. The process of claim 10 wherein the dispersing agent is selected from the group consisting alumina, Li$_2$CO$_3$, diatomaceous earth and sand or combinations thereof.

14. The process of claim 10 wherein the pH is from about 9.5 to about 10.5.

15. A process for preparing a compound of the formula:

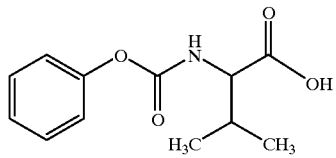

or a salt thereof, comprising reacting a compound of the formula:

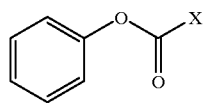

wherein X is Cl with a compound of the formula:

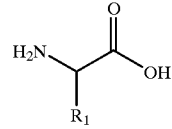

wherein R$_1$ is isopropyl, in the presence of LiOH and alumina at a pH of from about 9.5 to about 10.5.

* * * * *